United States Patent [19]

Svendsen

[11] 4,070,245
[45] Jan. 24, 1978

[54] SUBSTRATE FOR THE QUANTITATIVE DETERMINATION OF PROTEOLYTIC ENZYMES

[75] Inventor: Lars Gundro Svendsen, Reinach, Switzerland

[73] Assignee: Pentapharm A.G., Basel, Switzerland

[21] Appl. No.: 697,550

[22] Filed: June 18, 1976

[30] Foreign Application Priority Data

June 23, 1975 Switzerland .................. 8224/75

[51] Int. Cl.$^2$ .................. G01N 31/14; C07G 7/02
[52] U.S. Cl. .................. 195/99; 195/103.5 R; 260/112.5 R
[58] Field of Search ............. 195/103.5 R, 99, 66 R; 260/112.5 R

[56] References Cited

U.S. PATENT DOCUMENTS

| 3,884,896 | 5/1975 | Blomback et al. | ........ 195/103.5 R X |
| 3,886,136 | 5/1975 | Claeson et al. | ........... 195/103.5 R X |

OTHER PUBLICATIONS

Nachlas et al., Role Of Some Structural Features of Substrates On Trypsin Activity, Achives of Biochemistry and Biophysics, vol. 108, 1964, (pp. 266-274).
Plapinger et al., Synthesis of Chromogenic Arginine Derivatives as Substrates for Trypsin, J. Org. Chem., vol. 30, No. 6, 1965.
Buletza, Jr., et al., Microfluorometry of Brain Trypsin--Like Activity and Trypsin Inhibition with N-Carbobenzoxydiglycyl-1-arginine-2-naphthylamide (GGANA); Enzyme, vol. 12, 1971, (pp. 311-321).

*Primary Examiner*—David M. Naff
*Attorney, Agent, or Firm*—Pennie & Edmonds

[57] ABSTRACT

A substrate for the quantitative determination of enzymes in human and mammal body fluids as well as in animal cell extracts and glandular venoms of cold-blooded animals, which has the structure

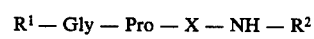

$$R^1 - Gly - Pro - X - NH - R^2$$

wherein $R^1$ represents hydrogen or a blocking acyl or sulfonyl group, $R^2$ represents an aromatic hydrocarbon group which may carry substituents and X represents arginyl or lysyl, —NH—$R^2$ being a chromogenic or fluorescent group capable of yielding a split product $NH_2$—$R^2$ the quantity of which can be measured by photometric, spectrophotometric or fluorescence-photometric methods.

18 Claims, 7 Drawing Figures

I: N$^\alpha$-Cbo-Gly-Pro-Arg-pNA·HCl
II: Bz-Phe-Val-Arg-pNA·HCl

I: $N^\alpha$-Cbo-Gly-Pro-Arg-pNA·HCl
II: Bz-Phe-Val-Arg-pNA·HCl

SUBSTRATE FOR THE QUANTITATIVE DETERMINATION OF PROTEOLYTIC ENZYMES

BACKGROUND OF THE INVENTION

The present invention relates to synthetic substrates which are to be used as reagents for the quantitative determination of proteolytic enzymes of the class E.C. 3.4.4. which split peptide chains on the carboxyl side of arginine as well as of lysine in human and mammal body fluids as well as in animal cell extracts and in glandular venoms of cold-blooded animals by photometric, spectrophotometric and fluorescence-photometric methods.

The published German patent application DOS No. 2,322,116 discloses a synthetic substrate which is to be used for the quantitative determination of enzymes of class E.C. 3.4.4., especially thrombin, plasmin and trypsin (enzyme nomenclature: "E.C." is the abbreviation for "Enzyme Committee" of the "International Union of Biochemistry"). The said substrate has a tripeptide chain of formula H — Phe — Val — Arg — OH in which the N-terminal amino acid is blocked by an acyl group and the C-terminal amino acid is substituted with a chromogenic or fluorescent group which is eliminated by the hydrolytic action of the said enzymes. The split product thus formed can be determined quantitatively by photometry. From the quantity of the chromogenic split product formed per time unit the enzymatic activity can be measured. In the tripeptide chain Phe may be replaced e.g. by Ph.Gly, Tyr, 4-methoxy-Tyr or 4-methyl-Phe, Val e.g. by Ile, Leu, nor-Val, Ph.Gly or Phe, and Arg e.g. by Lys, homo-Arg or Orn.

The substrate disclosed in German patent application No. 2,322,116 comprises in the peptide chain at least two optically active amino acid fragments which tend to racemize during the synthetic stepwise building of the peptide chain according to the methods commonly used in peptide chemistry. The degree of the racemization depends on the reaction conditions applied in the syntheses and varies from batch to batch since it is practically impossible to reproduce accurately the same reaction conditions. The formation of even small quantities of the corresponding D-amino acids results in a significant reduction of the susceptibility of the substrate to the enzymes, especially thrombin. As was shown by L. Svendsen et al. [cf. Thromb. Res. 1, 267–278 (1972)] the replacement of L-phenylalanine by D-phenylalanine causes the susceptibility of the substrate to be reduced 160 times. A racemization degree of the N-terminal amino acid as low as 1% causes a reduction of 1.6% in the susceptibility of the substrate. This prior art substrate is, therefore, not suitable for the purpose of standardizing enzymes.

The problem to be solved by the invention consisted in synthetizing a substrate having a higher susceptibility to enzymes of class E.C. 3.4.4. and undergoing no racemization during synthesis. The new substrate was to be made suitable for the standardization of enzymes. By increasing the susceptibility of the substrate it was furthermore intended to reduce the sample quantities of biological test materials, such as blood samples or samples of other body fluids, required for the determination of enzymes. This is of practical importance since often only very small quantities of test material are available and since it is desirable to spare the human subjects, especially children and elderly persons, when taking samples, e.g., blood, cell or lymph samples. It was also aimed at simplifying the techniques of taking samples by the staff of hospitals and thus to save costs.

In order to solve the problems set forth above the following speculations were made. As was known, thrombin and thrombin-like enzymes, e.g. Reptilase ® which is a product prepared from snake venom, as well as plasmin split the free α"A" chain fragment from human fibrinogen with formation of the hexadecapeptide fibrinopeptide A and the tripeptide glycyl-prolyl-arginine [cf. Birgit Hessel et al. FEBS LETTERS 18, No. 2, p. 318–320 (1971)]. From this fact one might conclude that the structure of the said tripeptide is particularly susceptible to thrombin, thrombin-like enzymes and plasmin. It was further known that the tripeptide split from the α"A" chain fragment by thrombin and thrombin-like enzymes contains glycine as the N-terminal amino acid. This amino acid is particularly well suited for building up peptide chains since it cannot racemize. The above mentioned tripeptide furthermore contains proline as central amino acid. This amino acid, though optically active, is stabilized due to the fact that the asymmetric α-carbon atom is linked with the α-amino group by a propylene bridge in a five-membered ring so that a racemization can only take place under extremely severe conditions which are never encountered in the methods used in peptide syntheses. On the grounds of the preceding considerations the amino acids contained in the above mentioned tripeptide and other structurally similar non-racemizing amino acids were used for building up a new substrate which proved to be particularly suitable for the quantitative determination of certain enzymes.

BRIEF SUMMARY OF THE INVENTION

The substrates to which the invention relates have the following structure $$R^1 - Gly - Pro - X - NH - R^2 \qquad I$$

wherein $R^1$ represents hydrogen or a blocking acyl or sulfonyl group, $R^2$ represents an aromatic hydrocarbon group which may carry substituents and X represents an arginyl or lysyl group.

These new substrates are suitable for the quantitative determination of certain proteolytic enzymes of class E.C. 3.4.4. which split peptide chains on the carboxyl side of arginine as well as of lysine. Under the action of the said enzymes the group $-NH-R^2$ is hydrolytically split off from the substrate with formation of a split product $NH_2-R^2$ the quantity of which can be measured by photometric, spectrophotometric or fluorescence-photometric methods. The quantity of the product $NH_2-R^2$ formed per time unit is a measure for the enzyme activity from which the quantity of enzyme present in a given tested sample can be calculated.

The substrates of this invention have a substantially higher susceptibility to certain enzymes such as plasmin and trypsin than the substrates disclosed in German patent application No. 2,322,116, especially than $N^\alpha$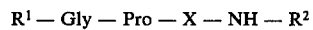—Bz—Phe—Val—Arg—pNA.HCl which is the prior art substrate having the highest susceptibility.

DETAILED DESCRIPTION OF THE INVENTION

Figure 1:
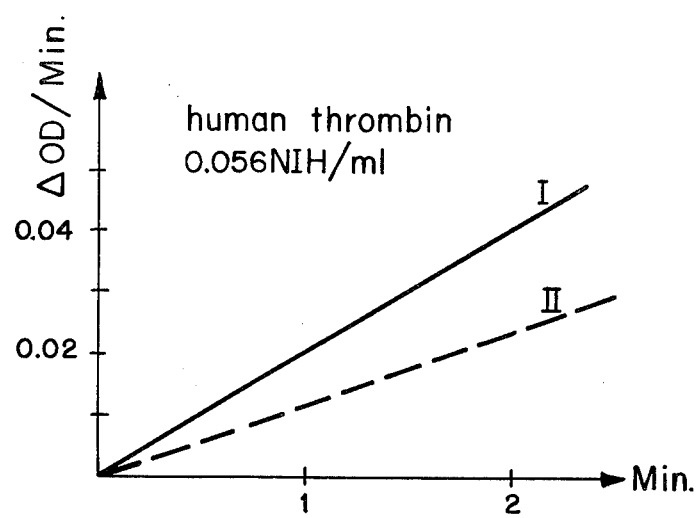
Figure 2:
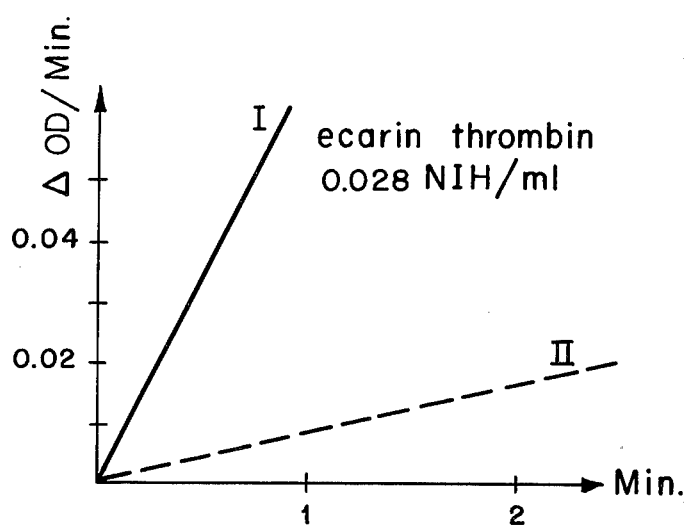
Figure 3:
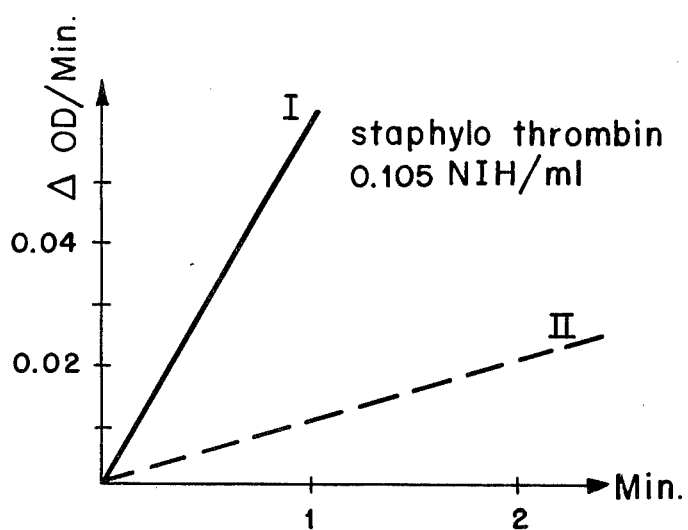
Figure 4:
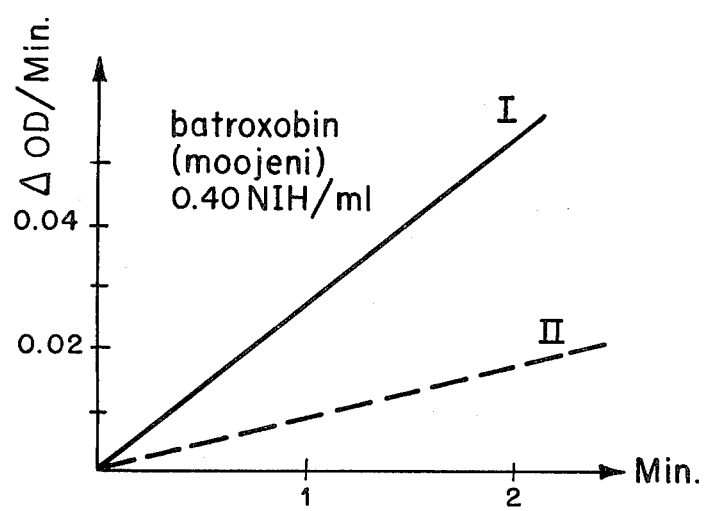
Figure 5:
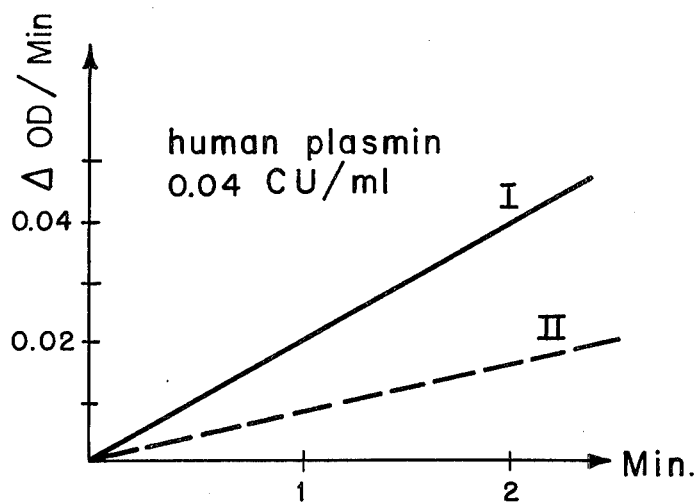
Figure 6:
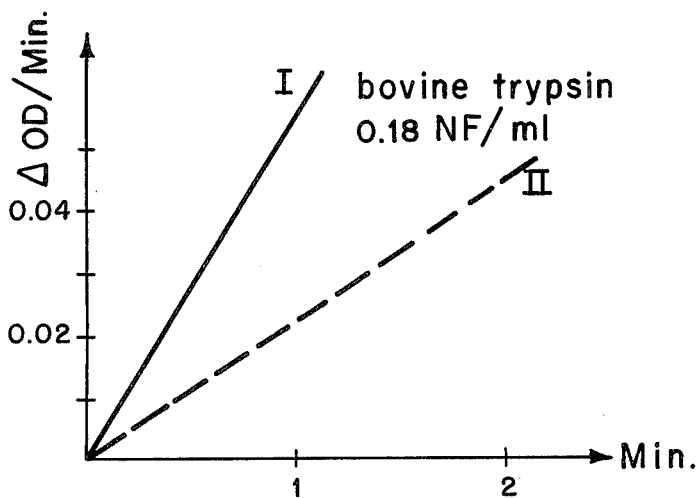

The acyl group represented by $R^1$ in the above formula I can be represented by the following partial formula $$R^3 - CO - \qquad \text{II}$$

wherein $R^3$ is a. an aliphatic hydrocarbon group having 1 to 17, preferably 1 to 8 carbon atoms, b. an araliphatic hydrocarbon group the aliphatic radical of which contains 1 to 6 carbon atoms, c. a cycloaliphatic hydrocarbon group, d. an aromatic hydrocarbon radical, e. an alkoxy group having 1 to 17, preferably 1 to 6 carbon atoms, or f. a benzyloxy group.

In particular $R^3$ can be a straight or branched alkyl radical such as methyl, ethyl, propyl, butyl, isobutyl, pentyl, hexyl, heptyl, octyl, etc. up to heptadecyl. $R^3$ can furthermore be a benzyl, 2-phenylethyl, 3-phenylpropyl, etc. up to 11-phenylundecyl radical. $R^3$ can also be a cyclohexyl, phenyl, α-naphthyl, β-naphthyl or biphenyl radical. Finally $R^3$ can be a methyloxy, ethyloxy, propyloxy, butyloxy, isobutyloxy, etc. up to heptadecyloxy group.

The sulfonyl group represented by $R^1$ in formula I can be an alkanesulfonyl group the alkane radical of which has 1 to 17, preferably 1 to 6 carbon atoms, e.g. a methane or ethanesulfonyl group, or an arylsulfonyl group the aromatic nucleus of which may carry one or more (e.g. three) lower alkyl substituents, e.g. a benzene, p-toluene or naphthalenesulfonyl group.

$R^2$ can be e.g. a p-nitrophenyl, 2-naphthyl or 4-methoxy-2-naphthyl group.

The substrates of the invention can be protonized with a mineral acid, e.g. HCl, HBr, $H_2SO_4$ or $H_3PO_4$, or an organic acid, e.g. formic, acetic, oxalic or tartaric acid.

A subclass of the substrates defined by formula I corresponds to the following formula

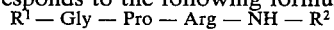
$$R^1 - Gly - Pro - Arg - NH - R^2 \qquad \text{III}$$

wherein $R^1$ represents an alkyloxycarbonyl group the alkyl radical of which has 1 to 6 carbon atoms, an aralkyloxycarbonyl group the alkylene radical of which has 1 to 6 carbon atoms, an alkanesulfonyl group the alkyl radical of which has 1 to 6 carbon atoms, an arylsulfonyl group the aryl radical of which may carry substituents, e.g. lower alkyl radicals such as methyl or ethyl, or an alkanoyl group the alkane portion of which has 1 to 6 carbon atoms, and $R^2$ represents a p-nitrophenyl, 2-naphthyl or 4-methoxy-2-naphthyl group.

The substrates of formula III have a high susceptibility not only to plasmin and trypsin but also to thrombin and thrombin-like enzymes.

The invention further relates to a method for quantitatively determining proteolytic enzymes of the class E.C. 3.4.4. which split peptide chains on the carboxyl side of arginine as well as of lysine, e.g. thrombin and thrombin-like enzymes, ecarin thrombin, plasmin and plasmin-like enzymes, trypsin, and indirectly proenzymes, proenzyme activators and enzyme inhibitors in human and mammal body fluids as well as in animal cell extracts and glandular venoms of cold-blooded animals such as snakes, which comprises reacting the said body fluids, cell extracts or venoms with a substrate of formula I and measuring photometrically, spectrophotometrically or fluorescence-photometrically the quantity of the product $NH_2-R^2$ formed by the hydrolytic action of the enzymes on the said substrate.

The substrates of the invention can be prepared by the following methods:

1. According to the first method the chromogenic groups ($R^2$ in formula I) are attached to the C-terminal amino acid group. These chromogenic groups at the same time protect the C-terminal carboxyl groups during the step-wise attachment of the amino acids in the process of building up the peptide chain. The other protecting groups are selectively eliminated from the end product without the chromogenic group being affected. This method is described e.g. in "Peptide Synthesis" by Miklos Bodansky et al., Interscience Publishers, 1966, p. 163–165.

2. According to the second method the chromogenic group is coupled to the finished peptide chain after removal of the other protective groups. In this case the C-terminal carboxy group is liberated by a reacemization-free enzymatic ester splitting. The esterolytic enzymes can be used as such or in combination with a matrix.

For protecting the $N^\alpha$-amino groups during the step-wise synthesis of the peptide chain usual protective groups known to protect amino groups and to be split off selectively can be used. These protecting groups include in the first place Cbo, MeOCbo, $NO_2$Cbo, MCbo, BOC, TFA and formyl. The α-carboxy group of the amino acids can be activated by several known methods, e.g. by preparing the p-nitrophenyl ester, pentachlorophenyl ester, or N-hydroxysuccinimide ester derivatives and isolating these derivatives, or by preparing in situ the acid azides or anhydrides which may be either symmetrical or asymmetrical.

The activation of the carboxy group can also be achieved by means of a carbodiimide such as N,N'-dicyclohexylcarbodiimide.

The C-terminal carboxy group in the peptide derivatives is protected during the step-wise synthesis of the required peptide chain by means of the chromogenic amide group or by conversion into the methyl, ethyl or isopropyl ester.

The other active free groups which do not participate in the synthesis of the peptide chain can be blocked by known methods. Thus, the δ-guanidino group of arginine may be protected by $NO_2$ or Tos or simply by protonization, whereas the ε-amino group of lysine may be protected by a Cbo, BOC or Tos group.

In the synthesis of the tripeptide chain it is convenient to proceed as follows: first attaching the blocking group (acyl or sulfonyl group) to the N-terminal amino acid, then activating the carboxyl group of the blocked amino acid and finally attaching the obtained activated amino acid derivative to the dipeptide derivative required for completing the peptide chain.

The preparation of the substrates of the invention is described in a more detailed manner in the following Examples.

The analysis of the eluates and products obtained according to the Examples was performed by thin layer-chromatography using glass plates coated with silica gel F 254 (Merck). The thin layer chromatograms were developed by means of the following solvent systems:

A—chloroform/methanol (9 : 1)
B—n-propanol/ethyl acetate/water (7 : 1 : 2)
C—n-butanol/acetic acid/water (3 : 1 : 1).

The abbreviations used in the present specification and claims have the following meaning:

Arg = L-arginine
Gly = glycine
Lys = lysine
Pro = L-proline

Ac = acetyl
AcOH = acetic acid
BOC = tert.-butoxycarboxyl
Bz = benzoyl
Bzl = benzyl
Bz$_2$O = benzoic anhydride
Cbo = carbobenzoxy
DMF = dimethylformamide
TLC = thin layer chromatogram
Et$_3$N = triethylamine
HMPTA = N,N,N',N',N'',N''-hexamethylphosphoric acid triamide
SS = solvent system
MeOH = methanol
NA = naphthylamide
OMe = methoxy
OpNP = p-nitrophenoxy
pNA = p-nitroanilide
2-NA = 2-naphthylamide
m.p. = melting point
THF = tetrahydrofuran
Tos = p-toluenesulfonyl Unless otherwise stated, all amino acids in the peptide chains have the L-form.

EXAMPLE 1

I. N$^\alpha$-Cbo-Gly-Pro-Arg-pNA.HCl

Ia. Cbo-Arg-pNA.HCl. In a 250ml three-necked flask 16.0 g (47.0 mmoles) of Cbo-Arg-OH.HCl, which had been dried in vacuo over P$_2$O$_5$, were dissolved in 90 ml of absolute HMPTA at 20° C, while keeping the atmosphere in the flask moisture-free. To the resulting solution were added at room temperature first a solution of 4.74 g (47.0 mmoles) of Et$_3$N in 10 ml of HMPTA and then portionwise 16.4 g (100 mmoles) of p-nitrophenylisocyanate (100% excess). After 24 hours' reaction time at 20° C most of the HMPTA was distilled off in vacuo. The residue was extracted several times with 30% AcOH. The residue was discarded. The combined acetic acid extracts were further purified by being passed through a column of "Sephadex G-15" equilibrated with 30% AcOH and eluted with 30% AcOH. That fraction of the acetic acid eluate which was split by treatment with trypsin with liberation of p-nitroaniline was freeze-dried. There were thus obtained 12.6 g of an amorphous powder which was homogeneous according to TLC in the SS C. Elementary analysis and calculation from the empirical formula C$_{20}$H$_{25}$N$_6$O$_5$Cl gave the following values: C = 51.29% (52.67%), H = 5.48% (5.42%), N = 17.92% (18.08%), Cl = 7.50% (7.63%).

I. N$^\alpha$-Cbo-Gly-Pro-Arg-pNA.HCl 4.65 g (10 mmoles) of compound Ia were treated, while stirring, with 40 ml of 2N HBr in glacial acetic acid for 1 hour at 20° C. The peptide derivative dissolved with CO$_2$ evolution. The reaction solution was added dropwise, while vigorously stirring, to 250 ml of absolute ether. This resulted in the precipitation of (2 HBr).H-Arg-pNA. The ethereal phase was sucked off and then the solid phase was washed four times with portions of 100 ml of absolute ether in order to remove the benzyl bromide which had formed as well as excess HBr and AcOH. After drying in vacuo over NaOH platelets the deblocked product was obtained in a quantitative yield. The dry (2 HBr).H-Arg-pNA was dissolved in 25 ml of DMF. After cooling of the solution to −10° C, 1.40 ml (10 mmoles) of Et$_3$N were added thereto. A precipitate of Et$_3$N.HBr formed which was filtered off and washed with a small quantity of cold DMF. 4.70 g (11 mmoles) of Cbo-Gly-Pro-OpNP were added to the filtrate at −10° C. After a few hours the reaction solution had reached 20° C. The solution was again cooled to −10° C and buffered with 0.35 ml (2,5 mmoles) of Et$_3$N. After 16 more hours a further 0.35 ml of Et$_3$N was added at −10° C. After further 24 hours the reaction solution was concentrated to dryness in vacuo at 40° C. The residue was dissolved in 50 ml of MeOH. After the addition of 0.8 ml (10 mmoles) of conc. HCl the solution was concentrated to dryness in vacuo at 20° C. This operation was repeated three times in order to convert the tripeptide hydrobromide into the hydrochloride. The crude tripeptide hydrochloride was dissolved in 50 ml of MeOH and pre-purified by gel filtration on a column of "Sephadex LH-20" equilibrated with MeOH. For a further purification that fraction of the MeOH eluate which was split by treatment with trypsin with liberation of p-nitroaniline was concentrated in vacuo. The residue was dissolved in 30% AcOH. The solution was purified by gel filtration on a column of "Sephadex G-15" equilibrated with 30% AcOH. That fraction of the AcOH eluate which was split by treatment with trypsin with liberation of p-nitroaniline was freeze-dried after addition of 0.80 ml (10 mmoles) of conc. HCl. There were thus obtained 3.64 g (58.8% of the theory) of an amorphous light powder which was homogeneous according to TLC in SS C. Elementary analysis and calculation from the empirical formula C$_{27}$H$_{35}$N$_8$O$_7$Cl gave the following values (the values from the empirical formula are put within brackets): C = 52.09% (52.38%), H = 5.83% (5.70%), N = 18.33% (18.10%), Cl = 5.75% (5.73%).

The amino acid analysis confirmed the expected presence of amino acids in the correct proportions: Arg: 0,96 — Gly: 1,00 — Pro: 0,96.

EXAMPLE 2

II. H-Gly-Pro-Arg-pNA.2HCl 61.91 g (0,1 mole) of compound I, prepared according to Example 1, were treated, while stirring, with 300 ml of 3N HCl in glacial acetic acid for 2 hours at 35° C. The peptide derivative dissolved with CO$_2$ evolution. The reaction solution was added dropwise, while vigorously stirring, to 2 liters of absolute ether. This resulted in the precipitation of flocculent H-Gly-Pro-Arg-pNA.2HCl. The ethereal phase was sucked off, and then the solid phase was washed four times with portions of 0.5 liter of absolute ether in order to remove the benzyl chloride formed as split product as well as the excess HCl and AcOH. After drying in vacuo over NaOH platelets the deblocked product was obtained in a quantitative yield. For further purification the dried product was dissolved in 900 ml of 30% AcOH. The solution was purified by gel filtration on a column of "Sephadex G-15" equilibrated with 30% AcOH. Thereby the AcOH eluate was divided into two fractions both of which were split by treatment with trypsin with liberation of p-nitroaniline. The main fraction contained the desired product and the minor fraction the starting material used. After the addition of 8 ml (0.1 mole) of conc. HCl to the main fraction the latter was freeze-dried. There were thus obtained 43.5 g (83.4% of the theory) of an amorphous powder which was homogeneous according to TLC in the SS C. Elementary analysis and calculation from the empirical formula C$_{19}$H$_{30}$N$_8$O$_5$Cl$_2$ gave the following values: C = 43.38%

(43.77%), H = 5.88% (5.80%), N = 21.72% (21.49%), Cl = 13.41% (13.60%).

The amino acid analysis confirmed the presence of the expected amino acids in the correct proportions: Arg: 0.95 – Gly: 1.00 – Pro: 0.94.

EXAMPLE 3

III. $N^\alpha$-2-Phenylacetyl-Gly-Pro-Arg-pNA.HCl 2.09 g (4 mmoles) of compound II prepared according to Example 2 were dissolved in 25 ml of DMF. After cooling to −10° C 555 μl (4 mmoles) of Et$_3$N and immediately afterwards 1.13 g (4.4 mmoles) of p-nitrophenyl phenylacetate (m.p. 61.5°–62° C) were added. The reaction mixture was further treated according to Example 1. Purification: Gel filtration on a column of "Sephadex G-15" equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 1.99 g (82.5% of the theory) of an amorphous powder which was homogeneous according to TLC in the SS C. Elementary analysis and calculation from the empirical formula $C_{27}H_{35}N_8O_6Cl$ gave the following values: C = 54.06% (53.77%), H = 5.78% (5.85%), N = 18.83% (18.58%), Cl = 5.79% (5.88%).

The amino acid analysis confirmed the presence of the expected amino acids in the correct proportions: Arg: 0.99 – Gly: 1.00 – Pro: 0.97.

EXAMPLE 4

IV. $N^\alpha$-3-Phenylpropionyl-Gly-Pro-Arg-pNA.HCl 2.09 g (4 mmoles) of compound II prepared according to Example 2 were dissolved in 25 ml of DMF. After cooling to −10° C 555 μl (4 mmoles) of Et$_3$N and immediately afterwards 1.19 g (4.4 mmoles) of p-nitrophenyl 3-phenylpropionate (m.p. 97°–98.5° C) were added. The reaction product was further treated according to Example 1. Purification: Gel filtration on a column of "Sephadex G-15" equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 2.06 g (83.5% of the theory) of an amorphous powder which was homogeneous according to TLC in the SS C. Elementary analysis and calculation from the empirical formula $C_{28}H_{37}N_8O_6Cl$ gave the following values: C = 54.25% (54.50%), H = 5.98% (6.04%), N = 18.29% (18.16%), Cl = 5.63% (5.75%).

The amino acid analysis confirmed the presence of the expected amino acids in the correct proportions: Arg: 1.02 – Gly: 1.00 – Pro: 0.98.

EXAMPLE 5

V. $N^\alpha$-Cyclohexylcarbonyl-Gly-Pro-Arg-pNA.HCl 2.09 g (4 mmoles) of compound II prepared according to Example 2 were dissolved in 25 ml of DMF. After cooling to −10° C 555 μl (4 mmoles) of Et$_3$N and immediately afterwards 1.10 g (4.4 mmoles) of p-nitrophenyl cyclohexylcarboxylate (m.p. 49°–50° C) were added. The reaction product was further treated according to Example 1. Purification: Gel filtration on a column of "Sephadex G-15" equilibrated with 30% AcOH. That fraction of the AcOH eluate which was split by treatment with trypsin with liberation of p-nitroaniline was freeze-dried after the addition of 320 μl (4 mmoles) of conc. HCl Yield: 1.87 g (78.6% of the theory) of an amorphous powder which was homogeneous according to TLC in SS C. Elementary analysis and calculation from the empirical formula $C_{26}H_{39}N_8O_6Cl$ gave the following values: C = 52.70% (52.47%), H = 6.72% (6.61%), N = 19.03% (18.83%), Cl = 5.83% (5.96%).

The amino acid analysis confirmed the presence of the expected amino acids in the correct proportions: Arg: 0.96 – Gly: 1.00 – Pro: 0.96.

EXAMPLE 6

VI. $N^\alpha$-Capryloyl-Gly-Pro-Arg-pNA.HCl 2.09 g (4 mmoles) of compound II prepared according to Example 2 were dissolved in 25 ml of DMF. After cooling to −10° C 555 μl (4 mmoles) of Et$_3$N and immediately afterwards 1.17 g (4.4 mmoles) of p-nitrophenyl caprylate were added. The reaction product was further treated according to Example 1.

Purification: gel filtration on a "Sephadex G-15" column equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 1.99 g (81.4% of the theory) of an amorphous powder which was homogeneous according to TLC in the SS C. Elementary analysis and calculation from the empirical formula $C_{27}H_{43}N_8O_6Cl$ gave the following values: C = 52.84% (53.06%), H = 7.15% (7.09%), N = 18.58% (18.34%), Cl = 5.73% (5.80%).

The amino acid analysis confirmed the presence of the expected amino acids in the correct proportions: Arg: 0.95 – Gly: 1.00 – Pro: 0.99.

EXAMPLE 7

VII. $N^\alpha$-Tos-Gly-Pro-Arg-pNA.HCl 2.09 g (4 mmoles) of compound II prepared according to Example 2 were dissolved in 25 ml of DMF. After cooling to −10° C 555 μl (4 mmoles) of Et$_3$N and immediately afterwards 840 mg (4.4 mmoles) of p-toluene sulfochloride (tosyl chloride) (m.p. 67°–69° C) were added. The reaction product was further treated according to Example 1.

Purification: gel filtration on a "Sephadex G-15" column equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 2.17 g (84.9% of the theory) of an amorphous powder which was homogeneous according to TLC in SS C. Elementary analysis and calculation from the empirical formula $C_{26}H_{35}N_8O_7SCl$ gave the following values: C = 48.50% (48.86%), H = 5.61% (5.52%), N = 17.73% (17.53%), S = 5.19% (5.02%), Cl = 5.49% (5.55%).

The amino acid analysis confirmed the presence of the expected amino acids in the correct proportions: Arg: 0.99 – Gly: 1.00 – Pro: 0.93.

EXAMPLE 8

VIII. $N^\alpha$-Benzenesulfonyl-Gly-Pro-Arg-pNA.NCl 2.09 g (4 mmoles) of compound II prepared according to Example 2 were dissolved in 25 ml of DMF. After cooling to −10° C 555 μl (4 mmoles) of Et$_3$N and immediately afterwards 780 mg (4.42 mmoles) benzenesulfochloride (m.p. 16°–17° C) were added. The reaction product was further treated according to Example 1.

Purification: gel filtration on a "Sephadex G-15" column equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 1.95 g (78.0% of the theory) of an amorphous powder which was homogeneous according to TLC in SS C. Elementary analysis and calculation from the empirical formula $C_{25}H_{33}N_8O_7SCl$ gave the following values: C = 47.79% (48.03%), H = 5.40% (5.32%), N = 18.11% (17.93%), S = 5.06% (5.13%), Cl = 5.61% (5.67%).

The amino acid analysis confirmed the presence of the expected amino acids in the correct proportions: Arg: 1.01 – Gly: 1.00 – Pro: 0.96.

EXAMPLE 9

IX. $N^\alpha$-Methanesulfonyl-Gly-Pro-Arg-pNA.HCl 2.09 g (4 mmoles) of compound II prepared according to Example 2 were dissolved in 25 ml of DMF. After cooling to −10° C 555 μl (4 mmoles) of Et₃N and immediately afterwards 345 μ(4.44 mmoles) of methanesulphochloride were added. The reaction product was further treated according to Example 1.

Purification: gel filtration on a "Sephadex G-15" column equilibrated with 30% AcOH. That fraction of the AcOH eluate which was split by treatment with trypsin with liberation of p-nitroaniline were freeze-dried after the addition of 320 μl (4 mmoles) of conc. HCl. Yield: 1.70 g (75.5% of the theory) of an amorphous powder which was homogeneous according to TLC in SS C. Elementary analysis and calculation from the empirical formula $C_{20}H_{31}N_8O_7SCl$ gave the following values: C = 42.88% (42.66%), H = 5.63% (5.55%), N = 20.08% (19.90%), S = 5.62% (5.70%), Cl = 6.21% (6.30%).

The amino acid analysis confirmed the presence of the expected amino acids in the correct proportions: Arg: 0.99 – Gly: 1.00 – Pro: 0.96.

EXAMPLE 10

X. $N^\alpha$-2-Naphthalensulfonyl-Gly-Pro-Arg-pNA.HCl 2.09 g (4 mmoles) of compound II prepared according to Example 2 were dissolved in 25 ml of DMF. After cooling to −10° C 555 μl (4 mmoles) of Et₃N and immediately afterwards 1,0 g (4.41 mmoles) of naphthalene-2-sulfochloride (m.p. 74°–76° C) were added. The reaction product was further treated according to Example 1.

Purification: gel filtration on a "Sephadex G-15" column equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 1.81 g (66.8% of the theory) of an amorphous powder which was homogeneous according to TLC in SS C. Elementary analysis and calculation from the empirical formula $C_{29}H_{35}N_8O_7SCl$ gave the following values: C = 51.88% (51.59%), H = 5.19% (5.23%), N = 16.75% (16.60%), S = 4.62% (4.75%), Cl = 5.12% (5.25%).

The amino acid analysis confirmed the presence of the expected amino acids in the correct proportions: Arg: 1.02 – Gly: 1.00 - Pro: 0.98.

EXAMPLE 11

XI. $N^\alpha$-Isobutyloxycarbonyl-Gly-Pro-Arg-p-Na.HCl 2.09 g (4 mmoles) of compound II prepared according to Example 2 were dissolved in 25 ml of DMF. After cooling to −10° C 555 μl (4 mmoles) of Et₃N and immediately afterwards 650 μl (5.0 mmoles) of isobutyl chloroformate were added. The reaction product was further treated according to Example 1.

Purification: gel filtration on a "Sephadex G-15" column equilibrated with 30% AcOH. That fraction of the AcOH eluate which was split by treatment with trypsin with liberation of p-nitroaniline was freeze-dried after the addition of 320 μl (4 mmoles) of conc. HCl. Yield: 1.71 g (73.1% of the theory) of an amorphous powder which was homogeneous according to TLC in SS C. Elementary analysis and calculation from the empirical formula $C_{24}H_{37}N_8O_7Cl$ gave the following values: C = 49.06% (49.27%), H = 6.42% (6.37%), N = 19.33% (19.15%), Cl = 5.98% (6.06%).

The amino acid analysis confirmed the presence of the expected amino acids in the correct proportions: Arg: 1.01 – Gly: 1.00 – Pro: 0.94.

EXAMPLE 12

XII. $N^\alpha$-Cbo-Gly-Pro-Arg-2-NA.HCl

XIIa. $N^\alpha$-Cbo-Arg(NO₂)-2-NA 3.53 g (10 mmoles) of well dried Cbo-Arg(No₂)-OH were dissolved in 150 ml of THF:DMF (3:1) in a moisture-free atmosphere. After cooling to −10° C 1.39 ml (10 mmoles) of Et₃N were added to the solution, and then 1.35 g (10 mmoles) of isobutyl chloroformate dissolved in 20 ml of THF were added dropwise within 15 minutes, the temperature being maintained between −10° C and −5° C. To the resulting solution was added dropwise a solution of 1.72 g (12 mmoles) of β-naphthylamine in 15 ml of THF, the above mentioned temperature still being maintained. The reaction mixture was allowed to stand for 24 hours at room temperature. The solvent was distilled off in vacuo and the residue was digested successively three times with dist. water, three times with 5% NaHCO₃ solution and again three times with distilled water. After drying in vacuo the crude product was dissolved in MeOH and subjected to chromatography on a column of "Sephadex LH-20" equilibrated with MeOH. From one fraction of the eluate there were obtained 3.75 g of the crystalline compound XIIa (78.4% of the theory) of m.p. 173°–174.5° C which was homogeneous according to TLC in the SS A and B. Elementary analysis and calculation from the empirical formula $C_{24}H_{26}N_6O_5$ gave the following values: C = 60.82% (60.24%), H = 5.63% (5.48%), N = 17.48% (16.72%).

XIIb. H-Arg-2-Na.HCl 957 mg (2 mmoles) of compound XIIa were weighed in the reaction vessel of a Sakakibara apparatus. 15 ml of dry hydrofluoric acid gas were condensed in the reaction vessel. The reaction was allowed to proceed for 1 hour at 0° C, while stirring, and resulted in the removal of the protective arginine nitro group as well as the carbobenzoxy group. The condensed hydrofluoric acid gas was removed from the reaction mixture by distillation in vacuo, and the residue was dissolved in DMF. In order to convert the amino acid derivative into the HCl salt 0.5 ml (∼ 6 mmoles) of conc. HCl was added and the solution concentrated to dryness. After having repeated twice these operations the residue was dissolved in 50 ml of 40% AcOH. The AcOH solution was purified on a column of "Sephadex G-15" equilibrated with 30% AcOH and eluted with 30% AcOH. That fraction of the AcOH eluate which was split by treatment with trypsin with liberation of p-nitroaniline was freeze-dried after the addition of 320 μl (4 mmoles) of conc. HCl. Yield: 473 mg (63.5% of the theory) of an amorphous powder which was homogeneous according to TLC in SS C. Elementary analysis and calculation from the empirical formula $C_{16}H_{23}N_5OCl_2$ gave the following values: C = 51.82% (51.62%), H = 6.18% (6.23%), N = 17.08% (18.81%), Cl = 18.75% (19.05%).

XII. $N^\alpha$-Cbo-Gly-Pro-Arg-2-NA.HCl 372 mg (1 mmole) of compound XIIb were treated according to Example 1 with 470 mg (1.1 mmole) of Cbo-Gly-Pro-OpNP in order to form compound XII. Purification: gel filtration on a column of "Sephadex G-15" equilibrated with 30% AcOH. That fraction of the AcOH eluate which was split by treatment with trypsin with liberation of β-naphthylamine was freeze-dried after the addition of 80 μl (1 mmole) of conc. HCl. Yield: 425 mg (68.1% of the theory) of an amorphous powder which was homogeneous according to TLC in SS C. Elementary analysis and calculation from the empirical formula $C_{31}H_{38}N_7O_5Cl$ gave the following values: C = 60.11% (59.65%), H = 6.25% (6.14%), N = 16.07% (15.71%), Cl = 5.59% (5.68%).

The amino acid analysis confirmed the presence of the expected amino acids in the correct proportions: Arg: 0.98 - Gly: 1.00 - Pro: 0.97.

EXAMPLE 13

XIII. $N^\alpha$-Tos-Gly-Pro-Arg-2-NA.HCl 625 mg (1 mmole) of compound XII (Example 12) were deblocked according to Example 2 and dissolved in 8 ml of DMF. After cooling to −10° C 140 μl (1 mmole) of $Et_3N$ and immediately afterwards 210 mg (1.1 mmole) of p-toluene-sulfochloride (m.p. 67°–69° C) were added. The reaction product was further treated according to Example 1.

Purification: gel filtration on a column of "Sephadex G-15" equilibrated with 30% AcOH. That fraction of the AcOH eluate which was split by treatment with trypsin with liberation of β-naphthylamine was freeze-dried after the addition of 80 μl (1 mmole) of conc. HCl. Yield: 500 mg (77.6% of the theory) of an amorphous powder which was homogeneous according to TLC in SS C. Elementary analysis and calculation from the empirical formula $C_{30}H_{38}N_7O_5$ SCl gave the following values: C = 56.13% (55.93%), H = 5.86% (5.95%), N = 15.48% (15.22%), S = 5.07% (4.98%), Cl = 5.39% (5.50%).

The amino acid analysis confirmed the presence of the expected amino acids in the correct proportions: Arg: 0.95 - Gly: 1.00 - Pro: 0.96.

EXAMPLE 14

XIV. $N^\alpha$-Cbo-Gly-Pro-Arg-4-MeO-2-NA.HCl
XIVa. $N^\alpha$-Cbo-Arg($NO_2$)-4-MeO-2NA 2.17 g (12.5 mmoles) of 4-methoxy-2-naphthylamine were reacted with 3.53 g (10 mmoles) of CbO-Arg($NO_2$)-OH. The reaction product was treated according to Example 12, par. XIIa. Purification: gel filtration on a column of "Sephadex LH-20" equilibrated with MeOH. From a fraction of the eluate there were obtained 3.35 g (65.9% of the theory) of the partially crystalline compound XIVa which was homogeneous according to TLC in the SS A and B. Elementary analysis and calculation from the empirical formula $C_{25}H_{28}N_6O_6$ gave the following values: C = 59.18% (59.05%), H = 5.43% (5.55%), N = 16.49%, (16.23%).

XIVb. H-Arg-4-MeO-2-NA.2HCl 1.02 g (2 mmoles) of compound XIVa were reacted according to Example 12, paragraph XIIb in order to form compound XIVb. Purification: gel filtration on a column of "Sephadex G-15" equilibrated with 30% AcOH. That fraction of the AcOH eluate which was split by treatment with trypsin with liberation of 4-methoxy-2-naphthylamine was freeze-dried after the addition of 320 μl (4 mmoles) of conc. HCl. Yield: 570 mg (71.0% of the theory) of an amorphous powder which was homogeneous according to TLC in SS C. Elementary analysis and calculation from the empirical formula $C_{17}H_{24}N_5O_2Cl_2$ gave the following values: C = 51.08% (50.88%), H = 5.98% (6.03%), N = 17.75% (17.45%), Cl = 17.55% (17.67%).

XIV. $N^\alpha$-Cbo-Gly-Pro-Arg-4-MeO-2-NA.HCl 402 mg (1 mmole) of compound XIVb were treated with 470 mg (1.1 mmole) of Cbo-Gly-Pro-OpNP according to Example 1, paragraph I, in order to form compound XIV. Purification: gel filtration on a column of "Sephadex G-15" equilibrated with 30% AcOH. That fraction of the AcOH eluate which was split by treatment with trypsin with liberation of 4-methoxy-2-naphthylamine was freeze-dried after the addition of 80 μl (1 mmole) of conc. HCl. Yield: 493 mg (75.4% of the theory) of an amorphous powder which was homogeneous according to TLC in SS C. Elementary analysis and calculation from the empirical formula $C_{32}H_{40}N_7O_6Cl$ gave the following values: C = 59.01% (58.75%), H = 6.10% (6.16%), N = 15.19% (14.99%), Cl = 5.35% (5.42%).

The amino acid analysis confirmed the presence of the expected amino acids in the correct proportions: Arg: 1.02 - Gly: 1.00 - Pro: 0.95.

EXAMPLE 15

XV. $N^\alpha$-Tos-Gly-Pro-Arg-4-Me-O-2-NA.HCl 655 mg (1 mmole) of compound XIV prepared according to Example 14 were deblocked according to Example 2 and dissolved in 8 ml of DMF. After cooling to −10° C 140 μl (1 mmole) of $Et_3N$ and immediately afterwards 210 mg (1.1 mmole) of p-toluene-sulphochloride were added. The reaction product was further treated according to Example 1. Purification: gel filtration on a column of "Sephadex G-15" equilibrated with 30% AcOH. That fraction of the AcOH eluate which was split by treatment with trypsin with liberation of 4-methoxy-2-naphthylamine was freeze-dried after the addition of 80 μl (1 mmole) of conc. HCl. Yield: 465 mg (69.0% of the theory) of an amorphous powder which was homogeneous according to TLC in SS C. Elementary analysis and calculation from the empirical formula $C_{31}H_{40}N_7O_6SCl$ gave the following values: C = 55.75% (55.22%), H = 6.01% (5.98%), N = 14.89% (14.54%), S = 4.59% (4.76%), Cl = 5.16% (5.26%).

The amino acid analysis confirmed the presence of the expected amino acids in the correct proportions: Arg: 0.98 - Gly: 1.00 - Pro: 0.96.

EXAMPLE 16

XVI. $N^\alpha$-Tos-Gly-Pro-Lys-pNA.HCl
XVIa. $N^\alpha$-BOC-$N^\epsilon$-Cbo-Lys-pNA 19.0 g (50 mmoles) of compound $N^\alpha$-BOC-$N^\epsilon$-Cbo-Lys-OH were dissolved in 100 ml HMPTA and to the solution were added 5.06 g (50 mmoles) of $Et_3N$ and then 16.4 g (100 mmoles) of p-nitrophenyl isocyanate according to Example 1, paragraph Ia. After 24 hours' reaction the reaction solution was added dropwise, while stirring, to 1 liter of 2% NaHCO₃ solution. The precipitated product was filtered off and washed three times with portions of 0.5 liter of 2% NaHCO₃ solution, three times with portions of 0.5 liter of dist. water, three times with portions of 0.5 liter of 0.5N HCl and finally three times with portions of 0.5 liter of distilled water. The resulting product was dried in vacuo at 40° C and then twice extracted with 30 ml of DMF heated to 70° C so as to completely dissolve the desired product, whereas the by-product, N,N'-bis-p-nitrophenylurea, remained undissolved. The DMF solution was concentrated in vacuo at 40° C. The residue was dissolved in MeOH. By gel filtration on a column of "Sephadex LH-20" equilibrated with MeOH there were obtained 18.85 g (75.3% of the theory) of the crystalline compound XVIa of m.p. 125°-125.5° C which was homogeneous according to TLC in the SS A and B. Elementary analysis and calculation from the empirical formula $C_{25}H_{32}N_4O_7$ gave the following values: C = 60.49% (59.99%), H = 6.35% (6.44%), N = 11.48% (11.19%).

XVIb. N$^\alpha$-Tos-Gly-Pro-Lys($\epsilon$-Cbo)-pNA 1.5 g (3 mmoles) of compound XVIa were treated for 1 hour, while stirring, at 20° C in a moisture-free atmosphere with 20 ml of trifluoroacetic acid, whereby the amino acid derivative dissolved with evolution of $CO_2$. The reaction solution was slowly added, while vigorously stirring, to 150 ml of dry ether, H-Lys($\epsilon$-Cbo)-pNA.trifluoroacetate being precipitated. The ethereal phase was sucked off through a filter rod. The remaining precipitate was washed four more times with portions of 50 ml of dry ether in order to remove excess trifluoroacetic acid. Drying in vacuo over NaOH platelets gave the deblocked product in a quantitative yield. The dried amino acid derivative trifluoro acetate salt was dissolved in 15 ml of DMF. After cooling to −10° C 415 μl (3 mmoles) of Et₃N were added to the solution in order to liberate the amino acid derivative from the trifluoro acetate. 1.48 g (3.31 mmoles) of Tos-Gly-Pro-OpNP were added to the reaction mixture. The reaction product was further treated according to Example 1, paragraph I. Purification: gel filtration on a column of "Sephadex LH-20" equilibrated with MeOH. Yield: 1.77 g (83.2% of the theory) of an amorphous substance which was homogeneous according to TLC in the SS A and B. Elementary analysis and calculation from the empirical formula $C_{34}H_{40}N_6O_9S$ gave the following values: C = 57.95% (57.61%), H = 5.59% (5.69%, N = 12.27% (11.86%), S = 4.49% (4.52%).

XVI. N$^\alpha$-Tos-Gly-Pro-Lys-pNA.HCl 1.42 g (2 mmoles) of compound XVIb were deblocked according to Example 2, Purification: gel filtration on a column of "Sephadex G-15" equilibrated with 30% AcOH. That fraction of the AcOH eluate which was split by treatment with trypsin with liberation of p-nitroaniline was freeze-dried after the addition of 160 μl (2 mmoles) of conc. HCl. Yield: 1040 mg (85.1% of the theory) of an amorphous powder which was homogeneous according to TLC in SS C. Elementary analysis and calculation from the empirical formula $C_{26}H_{35}N_6O_7SCl$ gave the following values: C = 50.76% (51.10%), H = 5.68% (5.77%), N = 13.98% (13.75%), S = 5.19% (5.25%), Cl = 5.68% (5.80%).

The amino acid analysis confirmed the presence of the expected amino acids in the correct proportions: Lys: 0.99 : Gly: 1.00 - Pro- 0.96.

EXAMPLE 17

XVII. N$^\alpha$-Isobutoxycarbonyl-Gly-Pro-Lys-pNA.HCl

XVIIa. N$^\alpha$-BOC-Gly-Pro-Lys($\epsilon$-Cbo)-pNA 2.0 g (4 mmoles) of compound XVIa prepared according to Example 16 were deblocked according to Example 16, paragraph XVIb, and dissolved in 20 ml of DMF. After cooling to −10° C 555 μl (4 mmoles) of Et₃N and immediately afterwards 1.73 g (4.40 mmoles) of BOC-Gly-Pro-OpNP were added to the solution. The reaction product was further treated according to Example 1, paragraph I. Purification: gel filtration on a column of "Sephadex LH-20" equilibrated with MeOH. Yield: 2.20 g (84.0% of the theory) of an amorphous substance which was homogeneous according to TLC in the SS A and B. Elementary analysis and calculation from the empirical formula $C_{32}H_{42}N_6O_9$ gave the following values: V = 59.03% (58.70%), H = 6.46% (6.47%), N = 12.89% (12.84%).

XVIIb. N$^\alpha$-Isobutoxycarbonyl-Gly-Pro-Lys($\epsilon$Cbo)-pNA 1.31 g (2 mmoles) of compound XVIIa were deblocked according to Example 16, paragraph XVIb, and dissolved in 12 ml of DMF. After cooling to −10° C 280 μl (2 mmoles) of Et₃N and immediately afterwards 285 μl (2.2 mmoles) of isobutyl chloroformate were added to the solution. The reaction product was further treated according to Example 1, paragraph I. Purification: filtration on a column of "Sephadex LH-20" equilibrated with MeOH. Yield: 1.15 g (87.8% of the theory) of an amorphous substance which was homogeneous according to TLC in the SS A and B. Elementary analysis and calculation from the empirical formula $C_{32}H_{42}N_6O_9$ gave the following values: C = 58.01% (58.70%), H = 6.40% (6.47%), N = 12.99% (12.84%).

XVII. N$^\alpha$-Isobutoxycarbonyl-Gly-Pro-Lys-pNA.HCl 660 mg (1 mmole) of compound XVIIb were deblocked according to Example 2. Purification: gel filtration on a "Sephadex G-15" column equilibrated with 30% AcOH. That fraction of the AcOh eluate which was split by treatment with trypsin with liberation of p-nitroaniline was freeze-dried after the addition of 80 μl (1 mmole) of conc. HCl. Yield: 430 mg (77.2% of the theory) of an amorphous powder which was homogeneous according to TLC in SS C. Elementary analysis and calculation from the empirical formula $C_{26}H_{33}N_6O_6Cl$ gave the following values: C = 52.04% (51.75T), H = 6.82% (6.70%), N = 15.30% (15.09%), Cl = 6.18% (6.36%).

The amino acid analysis confirmed the presence of the expected amino acids in the correct proportions: Lys: 0.93 - Gly: 1.00 - Pro: 0.96.

EXAMPLE 18

XVIII. N$^\alpha$-Tos-Gly-Pro-Lys-2-NA.HCl

XVIIIa. N$^\alpha$-BOC-N$^\epsilon$-Cbo-Lys-2NA 1.90 g (5 mmoles) of compound of N$^\alpha$-BOC-N$^\epsilon$-Cbo-Lys-OH were reacted according to Example 12, paragraph XIIa, to form compound XVIIIa. Purification: gel filtration on a column of "Sephadex LH-20" equilibrated with MeOH. Yield : 1.60 g (63.3% of the theory) of an amorphous compound which was homogeneous according to TLC in the SS A and B. Elementary analysis and calculation from the empirical formula $C_{29}H_{35}N_3O_5$ gave the following values: C = 68.08% (68.89%), H = 7.03% (6.98%), N = 8.59% (8.32%).

XVIIIb. N$^\alpha$-Tos-Gly-Pro-Lys($\epsilon$-Cbo)-2NA 1.05 g (2 mmoles) of compound XVIIIa were deblocked according to Example 16, paragraph XVIb, and dissolved in 20 ml of DMF. After cooling to −10°

C 280 μl (2 mmoles) of Et₃N and immediately afterwards 985 mg (2.21 mmoles) of Tos-Gly-Pro-OpNP were added to the solution. The reaction product was further treated according to Example 1, paragraph I. Purification: gel filtration on a column of "Sephadex LH-20" equilibrated with MeOH. Yield: 1.11 g (77.7% of the theory) of an amorphous substance which was homogeneous according to TLC in the SS A and B. Elementary analysis and calculation from the empirical formula $C_{38}H_{43}H_5O_7S$ gave the following valus: C = 64.30% (63.94%), H = 5.98% (6.07%), N = 10.18% (9.81%), S = 4.35% (4.49%).

XVIII. $N^\alpha$-Toas-Gly-Pr-Lys-2-NA.HCl 715 mg (1 mmole) of compound XVIIb were deblocked according to Example 2. Purification: gel filtration on a column of "Sephadex G-15" equilibrated with 30% AcOH. That fraction of the AcOH eluate which was split by treatment with trypsin with liberation of 2-naphthylamine was freeze-dried after the addition of 80 μl (1 mmole) of conc. Hcl. Yield: 470 mg (76.3% of the theory) of an amorphous powder which was homogeneous according to TLC in SS C. Elementary analysis and calculation from the empirical formula $C_{30}H_{38}N_5O_5SCl$ gave the following values: C = 58.11% (58.48%), H = 6.15% (6.22%), N = 11.79% (11.37%), S = 5.13% (5.20%), Cl = 5.63% (5.75%).

The amino acid analysis confirmed the presence of the expected amino acids in the correct proportions: Lys: 0.94 - Gly: 1.00 - Pro: 0.98.

EXAMPLE 19

XIX. Nα-TOS-Gly-Pro-Lys--Tos-Gly-Pro-Lys--MeO-2-NA.HCl

XIXa. $N^\alpha$-BOC-Nε-Cbo-Lys-4-MeO-2-NA 1.90 g (5 mmoles) of compound $N^\alpha$-BOC-Nε-Cbo-Lys-OH were treated according to Example 12, paragraph XIIa, with 1.22 g (7 mmoles) of 4-methoxy-2-naphthylamine. Purification: gel filtration on a column of "Sephadex LH-20" equilibrated with MeOH. Yield: 1.82 g (68.0% of the theory) of an amorphous compound which was homogeneous according to TLC in the SS A and B. Elementary analysis and calculated from the empirical formula $C_{30}H_{37}N_3O_6$ gave the following values: C = 68.05% (67.27%), H = 6.83% (6.96%), N = 9.10% (7.85%).

XIXb. $N^\alpha$-Tos-Gly-Pro-Lys(ε-Cbo)-4-MeO-2-NA 1.07 g (2 mmoles) of compound XIXa were deblocked according to Example 16, paragraph XVIB, and dissolved in 20 ml of DMF. After cooling to −10° C 280 μl (2 mmoles) of Et₃N were added to the solution and immediately afterwards 985 mg (2.21 mmoles) of Tos-Gly-Pro-OpNP. The reaction product was further treated according to Example 1, paragraph I. Purification: gel filtration on a column of "Sephadex LH-20" equilibrated with MeOh. Yield: 895 mg (60.2% of the theory) of an amorphous substance which was homogeneous according to TLC in the SS A and B. Elementary analysis and calculation from the empirical formula $C_{39}H_{45}N_5O_8S$ gave the following values: C = 63.62% (62.97%), H = 6.02% (6.0%), N = 9.88% (9,42%), S = 4.21% (4.31%).

XIX. $N^\alpha$-Tos-Gly-Pro-Lys-4-MeO-2-NA.HCl 745 mg (1 mmole) of compound XIXb were deblocked according to Example 2. Purification: gel filtration on a column of "Sephadex G-15" equilbrated with 30% AcOH. That fraction of the AcOH eluate which was split by treatment with trypsin with liberation of 4-methoxy-2-naphthylamine was freeze-dried after the addition of 80 μl (1 mmole) of conc. HCl. Yield: 470 mg (72.7% of the theory) of an amorphous powder which was homogeneous according to TLC in the SS C. Elementary analysis and calculation from the empirical formula $C_{31}H_{40}N_5O_6SC$ gave the following values: C = 57.95% (57.62%), H = 6.31% (6.24%), N = 11.09% (10.84%), S = 4.88% (4.96%), Cl = 5.41% (5.49%).

The amino acid analysis confirmed the presence of the expected amino acids in the correct proportions: Lys: 1.03 - Gly: 1.00 - Pro: 0.97.

The chromatograms referred to in the above Examples were developed first in UV light (254 nm) and then by the chlorine/toluidine reaction (cf. G. Pataki: "Dunnschichtchromatographie in der Aminosaure- und Peptid-Chemie", Water de Gruyter & Co., Berlin, 1966, p. 125).

The substrates of formula I can be used for the quantitative determination of proteolytic enzymes of the class E.C. 3.4.4. which split peptide chains on the carboxyl side of arginine as well as lysine. This class includes, in particular, thrombin, thrombin-like enzymes, ecarin thrombin, plasmin, plasmin-like enzymes and trypsin. The substrates of this invention can also be used for indirectly determining proenzymes, e.g. prothrombin, plasminogen and trypsinogen; proenzyme activators and enzyme inhibitors, e.g. antithrombines such as heparin cofactor (antithrombin III) and thus indirectly also heparin, antiplasmin ($\alpha_2$-macroglobulin), trypsin inhibitors ($\alpha_1$-antitrypsin), aprotinin, soya bean trypsin inhibitors and plasmin inhibitors.

When proenzymes are completely activated by activators or activator mixtures, the equivalent quantity of enzyme is formed which can be measured as such. The measurement of the activator concentration is carried out indirectly by determining the velocity of the formation of the enzyme from the proenzyme. This velocity is proportional to he activator concentration.

The substrates of formula III are particularly suitable for the determination of thrombin and thrombinlike enzymes.

The substrates according to the invention, e.g. the substrate prepared according to Example 1, viz. $N^\alpha$-Cbp-Gly-Pro-Arg-pNA.HCl. were used for the quantitative determination of various enzymes in blood plasma. The determination was carried out by taking advantage of the fact that the split product $NH_2$-$R^2$ formed by enzymatic hydrolysis of the substrate has an UV spectrum which differs from that of the substrate and is shifted toward higher wave lengths. Thus, the substrate according to Example 1, i.e., $N^\alpha$-Cbo-Gly-Pro-Arg-pNA.HCl, has an absorption maximum at 302 nm (nanometer) and a molecular extinction coefficient of 12,920. The absorption of the substrate is practically nil at 405 nm. The split product $NH_2$—$R^2$ formed by the enzymatic hydrolysis of the substrate, viz. p-nitroaniline, has an absorption maximum at 380 nm and a molecular extinction coefficient of 13,200. At 405 nm the extinction coefficient is but moderately reduced, i.e. to 9,650.

The degree of the enzymatic hydrolysis of the substrate, which is proportional to the quantity of p-Nitroaniline formed, can be easily determined by spectrophotometric measurement at 405 nm. The presence of an excess of substrate exerts no disturbing effect on the measurement at 405 nm. The conditions are practically the same for the other substrates carrying a p-nitroanilino group as a chromogenic group. The spectrophotometric measurement was therefore, carried out in all cases at 405 nm.

$N^\alpha$-Cbo-Gly-Pro-Arg-pNA.HCl (substrate according to Example 1) has the important advantage of having a solubility in water (>4 mg/ml) which is 4 times higher than that of the prior art thrombin substrate Bz-Phe-Val-Arg-pNA.HCl disclosed in German patent application No. 2,322,116 (about 1 mg/ml). Due to this higher water solubility enzyme determinations can be carried out at a much broader concentration range. This is of particular importance in standardized biological test methods since in these cases extreme values can be determined accurately without the necessity of first diluting or concentrating biological samples. The saving of time thus achieved is essential in clinical practice where it is often necessary to obtain as quickly as possible extreme values for diagnostic purposes. If the substrte has a low solubility in water, it is not possible to obtain substrate saturation within the whole concentration range. If there is no substrate saturation, the results of the enzyme determination will deviate from the dose/activity curve, and this is very disadvantageous in standardized biological test methods.

The enzymatic hydrolysis reaction can be represented by the following scheme:

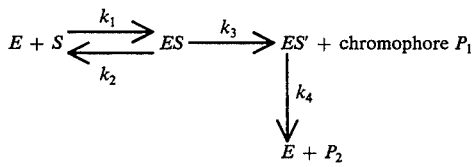

E = enzyme
S = substrte
ES = enzyme-substrate complex
$P_1$ and $P_2$ = products
$k_1 k_2$, $k_3$ and $k_4$ = rate constants
Dissociation constant for $$ES = \frac{k_2}{k_1} = K_m \text{ (Michaelis constant)}$$

If $[S] >> [E]$ and $k_4 << k_3$, the following is true:

$$K_m = \frac{([E] - [ES]) \cdot [S]}{[ES]} \quad (1)$$

The rate constant at which chromophore $P_1$ is formed is
$v = k_3 \cdot [ES]$ $$v = \frac{k_3 \cdot [E] \cdot [S]}{K_m + [S]} \quad (2)$$

If E is completely bound to S, then $[ES] = [E]$ and $$v = v_{max} = k_3 \cdot [E] \quad (3)$$

Lineweaver-Burk equation:

$$\frac{1}{v} = \frac{K_m}{v_{max}} \cdot \frac{1}{[S]} + \frac{1}{v_{max}} \quad (4)$$

As is evident from equation (2) constants $K_m$ and $k_3$ determine the activity of the enzyme substrate for a given enzyme. For determining these constants the following procedure is followed:

The enzyme and the substrate are mixed in a buffer solution, and the reaction is followed spectrophotometrically for 2 to 30 minutes. The concentration of substrate [S] is varied, whereas the enzyme concentration [E] is kept constant. If the extinction (OD) (= optical density) is plotted in a co-ordinate system as a function of time, a curve is obtained the tangent of which (difference in extinction per minute, $\Delta$ OD/minute, from which the quantity in $\mu$moles of pNA/min (v) can be calculated) at time zero corresponds to the ideal course of the hydrolysis. By means of this tangent the initial rate of the hydrolysis can be determined.

Figure 7:
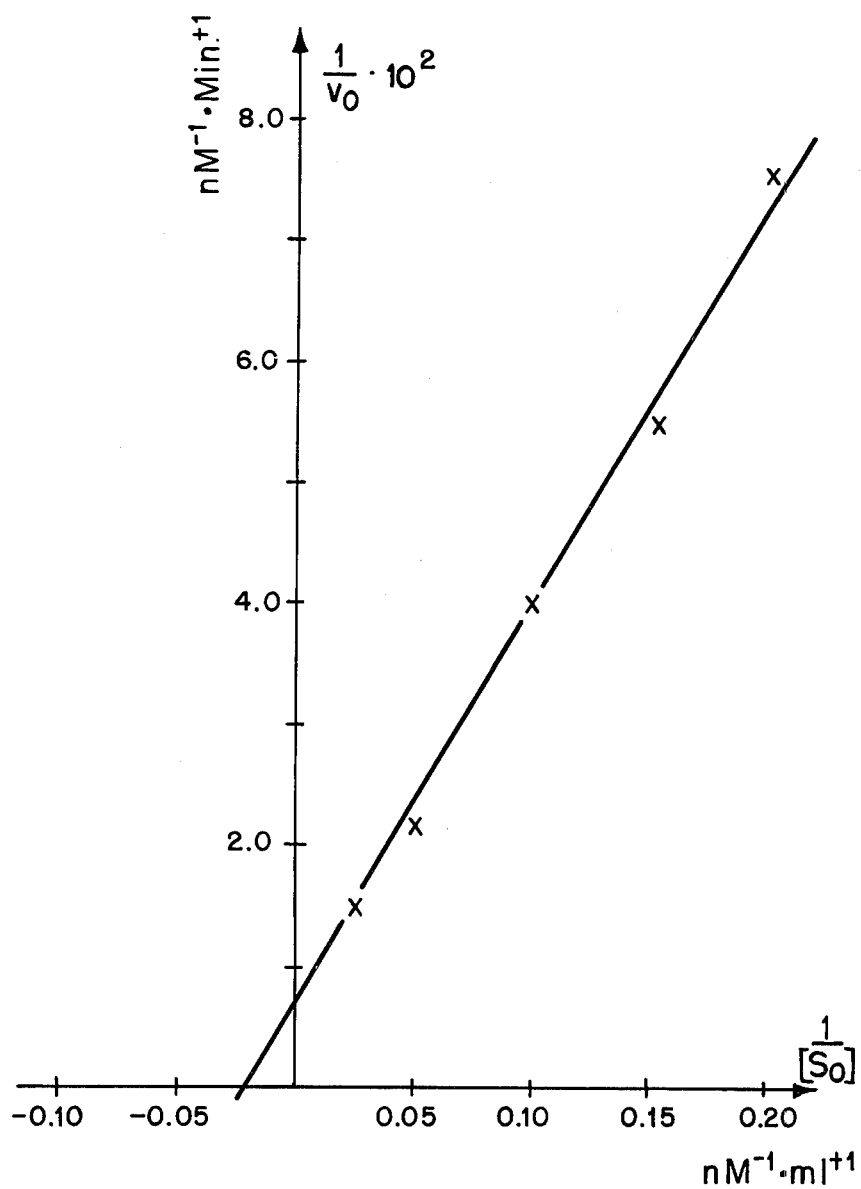

If $1/v$ is plotted against $1/[S]$, a Lineweaver-Burk diagram (cf. "Kurzes Lehrbuch der Biochemie" by P. KARSON, Georg Thieme-Verlag, Stuttgart, 1967., p. 70) is obtained from which $v_{max}$ and $K_m$ can be determined graphically.

$$K_m \text{ and } k_3 = \frac{v_{max}}{E}$$

were determined with $N^\alpha$-Cbo-Gly-Pro-Arg-pNA.HCl (substrate according to Example 1) for human thrombin, human plasmin and bovine trypsin. $K_m$ and $v_{max}$ were determined for the enzymes by means of the Lineweaver-Burk equation (the Lineweaver-Burk diagram is shown in FIG. 7 of the drawings attached to the specification). Since the enzymatic hydrolysis of the substrate by human thrombin follows the Michaelis-Menten law, it is possible to determine great variations in the thrombin quantity. According to the same principle $K_m$ and $v_{max}$ were determined for the other enzymes. The determined values are given in Table 3. All determinations were carried out in trisimidazole buffer at an ionic strength of 0.15 and a pH of 8.4 at 37° C.

In the drawings attached to this specification the Figures have the following meaning:

FIG. 1 to 6 are graphs in which the change in the optical density $\Delta$ OD caused by the hydrolytic action of human thrombin, ecarin-thrombin, human staphylo-thrombin, batroxobin (thrombin-like enzyme from Bothrops moojeni), human plasmin and bovine trypsin on substrate I (according to Example I) is plotted as a function of time in a coordinate system. For comparative purposes the change in the optical density caused by the action of the said enzymes on N$\alpha$-Bz-PheVal-Arg-pNA.HCl (substrate according to German patent application No. 2,322,116) is also plotted. All determinations were carried out in tris-imidazole buffer at an ionic strength of 0.15, a pH of 7.9 and a temperature of 37° C. The solutions of both substrates had the same molar concentration (1 $\mu$mole per ml).

FIG. 7 is a Lineweaver-Burk diagram for human thrombin.

The measurements the results of which are shown in FIG. 1 to 6 were carried out by the method described hereinafter.

0.25 ml of enzyme solution (0.56 NIH/ml of human thrombin, 0.28 NIH/ml of human ecarin-thrombin, 1.05 NIH/ml of human staphylo-thrombin, 4.0 NIH/ml of batroxobin, 0.4 CU/ml of human plasmin and 1.8 NF/ml of bovine trypsin) was added to 2.0 ml of tris-imidazole buffer (pH 8.4, ionic strength 0.15). The mixture was pre-incubated for 2 minutes at 37° C. Then, 0.25 ml of aqueous substrate solution (1 $\mu$mole of substrate I according to Example 1 and of $N^\alpha$-BzPhe-Val-Arg-pNA.HCl according to German patent application No. 2,322,116, respectively) was added to the pre-incubated mixture at 37° C. The increase in the absorption was measured spectrophotometrically at 405 nm and continuously followed by means of a recording device. The measuring results listed in Tables 1 and 2 were all obtained under the test conditions defined above. The quantity of the formed split product NH$_2$—R$^2$ is a measure for the susceptibility of the substrate to the enzymes. In the calculation of the quantity (nanomole) of p-nitroaniline formed per minute a molar extinction coefficient of 10,000 was used instead of 9,620, for the sake of simplifying. This had no influence on the relation between the susceptibilities of the various substrates to the enzymes. For determining the quantity (nanomole) of p-naphthylamine and 4-methoxy-β-naphthylamine (substrates XII to XV, XVIII and XIX), respectively, formed per minute the samples were irradiated in a fluorescence photometer with light having a wave length of 350 nm. The quantity of the formed split product was determined by measuring the intensity of the light emitted at 420 nm.

The susceptibility of the substrates prepared according to Examples 1 to 19 human thrombin, human plasmin and bovine trypsin can be read from Table 1.

TABLE 1

Activity of human thrombin, human plasmin and bovine trypsin, measured with the substrates of the invention at constant substrate and enzyme concentrations. For comparative purposes the corresponding values measured with N$^\alpha$-Bz-Phe-Val-Arg-pNA . HCl

| Substrate concentration 10$^{-4}$-molar | Quantity in nm of split product NH$_2$—R$^2$ released enzymatically within 1 minute by 1 NIH unit of human throbmin or 1 CU unit of human plasmin and 1 NF unit of bovine trypsin from the substrates | | |
|---|---|---|---|
| Substrate | human thrombin | human plasmin | bovine trypsin |
| N$^\alpha$-Bz-Phe-Val-Arg-pNA . HCl | 28.6 | 36.0 | 8.4 |
| I | 45.7 | 204.0 | 34.7 |
| II | 11.2 | 20.2 | 12.3 |
| III | 18.0 | 49.5 | 21.9 |
| IV | 21.3 | 60.8 | 24.8 |
| V | 2.4 | 33.8 | 28.5 |
| VI | 14.6 | 47.3 | 20.1 |
| VII | 73.8 | 195.5 | 26.1 |
| VIII | 65.8 | 111.0 | 27.5 |
| IX | 16.2 | 126.0 | 33.0 |
| X | 86.9 | 196.0 | 28.4 |
| XI | 43.8 | 93.5 | 25.3 |
| XII | 28.5 | 116.9 | 19.5 |
| XIII | 29.6 | 109.0 | 21.7 |
| XIV | 19.5 | 95.6 | 18.2 |
| XV | 25.9 | 125.0 | 28.6 |
| XVI | 0.9 | 192.6 | 22.9 |
| XVII | 0.85 | 150.8 | 26.1 |
| XVIII | 1.1 | 126.5 | 19.8 |
| XIX | 0.6 | 98.5 | 19.2 |

From Table 1 it can be seen that the substrates obtained according to Examples 1 to 19, except substrates II and V, have a significantly and in most cases substantially higher susceptibility to human plasmin than N$^\alpha$-Bz-Phe-Val-Arg-pNA.HCl. Without any exception, all of the listed substrates have a substantially higher susceptibility to bovine trypsin than the prior art substrate. From Table 1 it can furthermore be seen that the susceptibility of the substrates of the class including I, VII, VIII and XI to human thrombin is much higher than that of N$^\alpha$-Bz-Phe-Val-Arg-pNA.HCl.

TABLE 2

Activity of human ecarin-thrombin, human thrombin coagulase and batroxobin (thrombin-like enzyme from venom of Bothrops moojeni), measured by means of substrate I at constant substrate and enzyme concentrations. For comparison the corresponding values determined with N$^\alpha$-Bz-Phe-Val-Arg-pNA . HCl are indicated

| Substrate concentration 10$^{-4}$ M Substrate | Quantity in nanomoles of p-nitroaniline enzymatically split off from the substrate in 1 minute by the quantity of human ecarin-thrombin, human thrombin coagulase and batroxobin corresponding to 1 NIH | | |
|---|---|---|---|
| | Human ecarin-thrombin | human thrombin coagulase | batroxobin |
| N$^\alpha$-Bz-Phe-Val-Arg-pNA . HCl | 30.7 | 102 | 3.26 |
| I | 246.4 | 575 | 15.81 |

TABLE 3

K$_m$ and v$_{max}$ of various enzymes, determined by means of two substrates of the invention, i.e. N$^\alpha$-Cbo-Gly-Pro-Arg-pNA . HCl (I) and N$^\alpha$-Tos-Gly-Pro-Arg-pNA . HCl (VII) (graphically determined from the Lineweaver-Burk diagram according to FIG. 7 of the drawings)

| Enzyme | K$_m$ mole/liter | | v$_{max}$ μmole/liter | |
|---|---|---|---|---|
| | substrate I | substr.VII | substr.I | substr.VII |
| human thrombin | 5.71×10$^{-5}$ | 1.70×10$^{-5}$ | 5.34×10$^{-2}$ NIH | 7.57×10$^{-2}$ NIH |
| human plasmin | 3.57×10$^{-4}$ | 3.23×10$^{-4}$ | 67.3×10$^{-2}$ CU | 61.8×10$^{-2}$ CU |
| bovine trypsin | 2.70×10$^{-5}$ | 1.58×10$^{-5}$ | 4.27×10$^{-2}$ NF | 2.97×10$^{-2}$ NF |

DEFINITIONS

The thrombin NIH unit is that of the U.S. National Institute of Health, and the thrombin standard corresponds to the "US Standard Thrombin Lot B-3" (21.7 NIH/mg) published on March 3, 1973, by the Division of Biologics Standards of the National Institute of Health, Bethesda, Maryland 20014, USA.

The quantity of human ecarin-thrombin, human thrombin coagulase and batroxobin corresponding to the NIH unit is the quantity of enzyme which will clot a fibrinogen solution under standard conditions in the same time as does 1 NIH unit of standard thrombin. Test conditions: The mixture of 0.2 ml of solution of 1 NIH unit/ml of "US Standard Thrombin Lot B-3" in albumin buffer (pH 7.2) and 0.2 ml of 0.4% bovine fibrinogen solution in distilled water gives a clotting time of 20.2 seconds.

The plasmin CU unit is the casein unit which is measured on casein under standard conditions.

The trypsin NF unit is the quantity of enzyme which causes a change in the absorption Δ OD of 0.003 per minute, measured by means of benzoyl-L-arginine ethyl ester under standard conditions (cf. "The National Formulary XII" published by the American Pharmaceutical Association, Washington D.C., 1965, pages 417/418).

An enzyme unit is the quantity of enzyme which hydrolyzes 1 μmole of substrate in 1 minute at substrate saturation and at a given temperature, ionic strength and pH. One thousandth of this unit is a milli enzyme unit (m$^U$) which hydrolyzes 1 nanomole of substrate per minute under the conditions defined above.

One human thrombin unit (1 U), measured by means of substrate I (N$^\alpha$-Cbo-Gly-Pro-Arg-pNA.HCl) at a 1.5 × 10$^{-4}$ molar substrate concentration, a temperature of 37° C, an ionic strength of 0.15 and a pH of 8.4, corresponds to the quantity of 27.1 NIH units of human thrombin (1 milliunit = 0.0271 NIH unit, or 1 NIH unit = 36.9 milli-units).

By using the substrates of the invention it is possible to determine much smaller quantities of the said enzymes than with the prior art substrates. This is of utmost importance in clinical practice where often only small test samples are available or in cases where the concentrations of the enzymes, proenzymes, proenzyme activators or enzyme inhibitors to be determined are extremely low due to pathological conditions.

The substrates of the invention can also be used e.g., for determining prothrombin and antithrombin as will be shown hereafter.

For determining prothrombin 5 µl of citrated plasma ("Ci-Trol™ Normal" supplied by American Hospital Supply Corp., DADE division, Miami) was added to 0.5 ml of glycine buffer having a pH of 8.4 and an ionic strength of 0.3. The mixture was pre-incubated for 30 seconds at 37° C. Then, 100 µl of aqueous calcium thromboplastin (which is a prothrombin activator supplied by the firm Boehringer, Mannheim, Germany) were added to the pre-incubated mixture. The obtained mixture was incubated at 37° C. After an incubation time of 2 ¼ minutes the prothrombin activation was complete. After incubation times of more than 5 minutes part of the activated thrombin disappeared due to the action of antithrombins present in the plasma. After an incubation time of 4 minutes the said incubation mixture was mixed at 37° C with 1 ml of glycine buffer having a pH of 8.4 and an ionic strength of 0.3 and subsequently with 0.25 ml of a 1.5 × 10$^{-3}$ molar aqueous solution of substrate I. The course of the hydrolysis of the substrate was followed by photometrically measuring at 405 nm the quantity of p-nitroaniline formed per minute. The increase in the optical density was 0.162 per minute. From this valve and the molar extinction coefficient of 10,000 for p-nitroaniline at 405 nm the value of 5.99 mU for the thrombin formed from prothrombin was calculated. This meant that 5.99 units of substrate I thrombin had been formed from prothrombin, and that this corresponded to 162.3 NIH units of thrombin per ml of plasma.

For determining antithrombin 0.1 ml of an aqueous thrombin solution having a thrombin concentration varying between 25 and 40 NIH units per ml was added at 37° C to 1 ml of glycine buffer containing 3 USP units of heparin and having a pH of 8.4 and an ionic strength of 0.3. To the mixture there was added citrated plasma in quantities varying between 2.5 and 10 µl. The mixture was then incubated for 30 seconds at 37° C. Immediately after the incubation 0.25 ml of "Polybren" solution (concentration 1 mg of "Polybren" per 1 ml of 0.3 molar aqueous sodium chloride solution) was added to the mixture. ("Polybren" is a product which comprises 1,5-dimethyl-1,5-diazaundecamethylene-polymethobromide and which is supplied by Aldrich Chemical Company, Inc., Milwaukee, Wisconsin, USA). The obtained mixture was incubated for 30 seconds at 37° C. Afterwards 0.5 ml of a 0.75 × 10$^{-3}$ molar aqueous solution of substrate I was added to the mixture. The course of the hydrolysis of the substrate caused by the excess thrombin over the thrombin quantity neutralized by antithrombin was followed by photometrically measuring at 405 nm the quantity of p-nitroaniline formed per minute. It was found that inhibition of the added thrombin by various quantities of citrated plasma was proportional to these quantities.

TABLE 4

| | | | | |
|---|---|---|---|---|
| mIU per µl of plasma, calculated from the decrease Δ OD/min. caused by 10 µl of plasma | 6.14 | 6.60 | 6.51 | 6.42 |
| Δ OD/min, with 10 µl of plasma in the incubate | 0.505 | 0.405 | 0.305 | 0.180 |
| mIU per µl of plasma, calculated from the decrease Δ OD/min. caused by 7.5 µl of plasma | 6.22 | 6.69 | 6.56 | 6.32 |
| Δ OD/min. with 7.5 µl of plasma in the incubate | 0.584 | 0.490 | 0.390 | 0.270 |
| mIU per µl of plasma, calculated from the decrease Δ OD/min. caused by 5 µl of plasma | 6.31 | 6.38 | 6.31 | 6.38 |
| Δ OD/min. with 5 µl of plasma in the incubate | 0.665 | 0.588 | 0.485 | 0.353 |
| mIU per µl of plasma, calculated from the decrease Δ OD/min. caused by 2.5 µl of plasma | 6.30 | 6.59 | 6.45 | 6.22 |
| Δ OD/min. with 2.5 µl of plasma in the incubate | 0.750 | 0.671 | 0.568 | 0.441 |
| Δ OD/min. of the thrombin without plasma | 0.835 | 0.760 | 0.655 | 0.525 |
| Quantity of thrombin in NIH units used in the incubate | 4.16 | 3.78 | 3.26 | 2.61 | mIU = milli inhibitor units

From Table 4 it can be seen that variations in the quantity of thrombin present in the incubation mixture between 2.6 and 4.1 NIH units have no influence on the determination of antithrombin if the quantity of plasma is in the range of 2.5 to 10 µl. 6.40 ± 4% Substrate I inhibitor units were measured per µl of plasma. This corresponds to 6400 ± 4% substrate I milli inhibitor units per µl of plasma. In other words, this means that 1 ml of plasma inhibits 173.4 ± 4% NIH units of thrombin.

The substrates of the invention which contain Gly-Pro-Arg or Gly-Pro-Lys as the tripeptide chain have a much higher susceptibility to certain enzymes than the prior art substrates. This fact is very surprising if one takes into consideration the fact that prior to the present invention it was generally taken for granted, as can be seen from the scientific literature, that a substrate had necessarily to have a phenylalanine group in position 3 to an arginine group in position 1 in the peptide chain in order to have a maximum susceptibility to thrombin [cf. L. Svendsen et al., Thrombosis Research 1, 276 (1972)]. This theory is also supported by the fact that fibrinopeptide A is split much faster from human fibrinogen by thrombin than the tripeptide Gly-Pro-Arg. Fibrinopeptide A contains an L-phenylalanine group in the position 9 to the arginine group in position 1. However, since fibrinopeptide A forms an α-helix, as in generally assumed, the distance between the L-phenylalanine group and the arginine group is practically the same as in a stretched tripeptide chain containing the L-phenylargine group in position 3 to the arginine group in position 1 [cf. Blomback et al., Scand. J. Clin. Lab. Invest. 24, Suppl. 107, 59 (1969)].

I claim:

1. A chromogenic or fluorescent substrate for the quantitative determination of proteolytic enzymes of class E.C. 3.4.4. which split peptide chains on the carboxyl side of arginine and lysine in human and mammal body fluids, in animal cell extracts and in glandular venoms of cold-blooded animals, which has the structure $$R^1 - Gly - Pro - X - NH - R^2 \quad \quad I$$

wherein $R^1$ represents hydrogen or a blocking acyl or sulfonyl group, $R^2$ represents an aromatic hydrocarbon group which may carry substituents, and X represents an arginyl or lysyl group, $-NH-R^2$ being a chromogenic or fluorescent group, and which, when subjected to the proteolytic action of the said enzymes, yields a split product of formula $NH_2—R^2$ the quantity of which is measurable by photometric, spectrophotometric or fluoroescence-photometric methods.

2. The substrate according to claim 1 which is protonized with a mineral acid or an organic acid.

3. The substrate according to claim 1 in which the acyl group $R^1$ has the partial formula $$R^3 — CO —  \qquad \text{II}$$

wherein $R^3$ represents
a. an aliphatic hydrocarbon radical comprising 1 to 17 carbon atoms,
b. an araliphatic hydrocarbon radical the aliphatic group of which comprises 1 to 6 carbon atoms,
c. a cycloaliphatic hydrocarbon radical,
d. an aromatic hydrogen radical, or
e. an alkoxy group having 1 to 17 carbon atoms, or
f. a benzyloxy group.

4. The substrate according to claim 1 in which the sulfonyl group represented by $R^1$ is an alkanesulfonyl group the alkane radical of which has 1 to 17 carbon atoms or an arylsulfonyl group which can carry one or more lower alkyl substituents.

5. The substrate according to claim 1 in which $R^2$ is a p-nitrophenyl, 2-naphthyl or 4-methoxy-2-naphthyl group.

6. A chromogenic or fluorescent substrate for the quantitative determination of enzymes of glass E.C. 3.4.4. which split peptide chains on the carboxyl side of arginine and of lysine, especially thrombin and thrombin-like enzymes, in human and mammal body fluids, in animal cell extracts and in glandular venoms of cold-blooded animals, which has the structure $$R^1 — Gly — Pro — Arg — NH — R^2 \qquad \text{III}$$

wherein $R^1$ is an alkyloxycarbonyl group the alkyl radical of which has 1 to 6 carbon atoms, an aralkyloxycarbonyl group the alkylene group of which has 1 to 6 carbon atoms, an alkanesulfonyl group the alkane radical of which has 1 to 6 carbon atoms, an arylsulfonyl group the aryl radical of which may carry substituents, or an alkanoyl group the alkane radical of which has 1 to 6 carbon atoms, and $R^2$ is a p-nitrophenyl, 2-naphthyl or 4methoxy-2-naphthyl group.

7. $N^\alpha$-2-Naphthalenesulfonyl-glycyl-prolyl-arginine-p-nitroanilide hydrochloride.

8. $N^\alpha$-Tosyl-glycyl-propyl-arginine-p-nitroanilide hydrochloride.

9. $N^\alpha$-Benzenesulfonyl-glycyl-prolyl-arginine-p-nitroanilide hydrochloride.

10. $N^{60}$-Benzyloxycarbonyl-glycyl-prolyl-arginine-p-nitroanilide hydrochloride.

11. $N^\alpha$-Isobutyloxycarbonyl-glycyl-prolyl-arginine-p-nitroanilide hydrochloride.

12. The substrate according to claim 2 wherein the mineral acid is HCl, HBr, $H_2SO_4$ or $H_3PO_4$.

13. The substrate according to claim 2 wherein the organic acid is formic acid, oxalic acid or tartaric acid.

14. The substrate according to claim 4 wherein the alkanesulfonyl group is a methane or ethanesulfonyl group.

15. The substrate according to claim 4 wherein the arylsulfonyl group is a benzene, p-toluene or naphthalene-sulfonyl group.

16. A method for the quantitative determination of proteolytic enzymes of class E.C. 3.4.4. which split peptide chains on the carboxyl side of arginine and of lysine in human and mammal body fluids, in animal cell extracts and in glandular venoms of cold-blooded animals, which comprises reacting the said body fluids, cell extracts or glandular venoms with a substrate having the following structure $$R^1 — Gly — Pro — X — NH — R^2 \qquad \text{I}$$

wherein $R^1$ represents hydrogen or a blocking acyl or sulfonyl group, $R^2$, represents an aromatic hydrocarbon group which may carry substituents, and X represents an arginyl or lysyl group, $—NH—R^2$ being a chromogenic or fluorescent group, and measuring quantitatively by photometric, spectrophotometric or fluorescence-photometric methods the quantity of the split product $NH_2—R^2$ formed by the hydrolytic acid of the said enzymes on the substrate.

17. The method according to claim 16 wherein thrombin and thrombin-like enzymes, ecarin thrombin, plasmin and plasminlike enzymes, trypsin and indirectly proenzymes, proenzyme activators and enzyme inhibitors are quantitatively determined.

18. A method for the quantitative determination of thrombin and thrombin-like enzymes in human and mammal body fluids, in animal cell extracts and in glandular venoms of cold-blooded animals, which comprises reacting the said body fluids, cell extracts or glandular venoms with a substrate having the following structure.

$$R^1 —Gly — Pro — Arg — NH — R^2$$

wherein $R^1$ is an alkyloxycarbonyl group the alkyl radical of which has 1 to 6 carbon atoms, an aralkyloxycarbonyl group the alkylene group of which has 1 to 6 carbon atoms, an alkanesulfonyl group the alkane radical of which has 1 to 6 carbon atoms, an arylsulfonyl group the aryl radical of which may carry substituents, or an alkanoyl group the alkane radical of which has 1 to 6 carbon atoms, and $R^2$ is a p-nitrophenyl, 2-naphthyl or 4-methoxy-2-naphthyl group, and measuring quantitatively by photometric, spectrophotometric or fluorescence-photometric methods the quantity of the split product $NH_2—R^2$ formed by the hydrolytic action of the said enzymes on the substrate.

* * * * *

UNITED STATES PATENT AND TRADEMARK OFFICE
CERTIFICATE OF CORRECTION

PATENT NO. : 4,070,245 (page 1 of 2)
DATED : January 24, 1978
INVENTOR(S) : Lars Gundro Svendsen It is certified that error appears in the above-identified patent and that said Letters Patent are hereby corrected as shown below:

Column 2, line 59, reads "Nα$\lambda$" should read --Nα--

Column 5, line 49, reads "(52.67%), should read --(51.67%)--

Column 8, line 60, reads ".NCl", should read --.HCl--

Column 14, line 15, reads "V=59.03%", should read --C=59.03%--

Column 14, line 26, reads "filtration" should read
--gel filtration--

Column 14, line 46, reads "(51.75T)" should read --(51.75%)--

Column 15, line 10, reads "$C_{38}H_{43}H_5O_7S$" should read
--$C_{38}H_{43}N_5O_7S$--

Column 15, line 60 reads "(6.0%)" should read --(6.10%)--

UNITED STATES PATENT AND TRADEMARK OFFICE
CERTIFICATE OF CORRECTION

PATENT NO. : 4,070,245                                            (page 2 of 2)
DATED : Jnauary 24, 1978
INVENTOR(S) : Lars Gundro Svendsen It is certified that error appears in the above-identified patent and that said Letters Patent are hereby corrected as shown below:

Column 16, line 35, reads "he" should read --the--

Column 16, line 41, reads "Cbp" should read --Cbo--

Column 21, line 34, reads "valve" should read --value--

Column 23, line 55, reads "$N^{60}$", should read --$N^{\alpha}$--

Column 24, line 28, reads "acid" should read --action--

Signed and Sealed this

Twentieth Day of June 1978

[SEAL]

Attest:

RUTH C. MASON
*Attesting Officer*

DONALD W. BANNER
*Commissioner of Patents and Trademarks*